United States Patent [19]
Schilling

[11] Patent Number: 4,658,036
[45] Date of Patent: Apr. 14, 1987

[54] INVERT EMULSIFIERS FOR OIL-BASE DRILLING MUDS

[75] Inventor: Peter Schilling, Charleston, S.C.

[73] Assignee: Westvaco Corporation, New York, N.Y.

[21] Appl. No.: 783,692

[22] Filed: Oct. 3, 1985

[51] Int. Cl.[4] .......................................... C07D 209/48
[52] U.S. Cl. ................................... 548/513; 548/352; 564/138; 564/153; 564/159
[58] Field of Search ................ 548/513, 352; 564/138, 564/159, 153

[56] References Cited

U.S. PATENT DOCUMENTS 3,804,852  4/1974  Haemmerle et al. ............ 548/513 X
4,225,497  9/1980  Baudouin et al. ............... 548/513 X Primary Examiner—Richard A. Schwartz
Attorney, Agent, or Firm—Terry B. McDaniel; Richard L. Schmalz

[57] ABSTRACT

A process is disclosed for preparation of invert emulsifiers useful for oil-base drilling muds. The emulsifiers are prepared by reacting at least one tall oil fatty acid with acrylic acid, maleic anhydride or fumaric acid. The product of this reaction is substantially reacted with diethylene triamine, and at least one tall oil fatty acid to give the invert emulsifier.

17 Claims, No Drawings

INVERT EMULSIFIERS FOR OIL-BASE DRILLING MUDS

BACKGROUND OF THE INVENTION

The present invention relates to oil-base drilling fluids, and more particularly to invert water-in-oil emulsion drilling fluids in which the emulsifier is a reaction product of tall oil fatty acids.

In the drilling of wells by the rotary drilling technique, drilling fluid is circulated from tanks at the wellhead down the inside of the drill pipe, through the bit and back up the annulus. This patent application is directed specifically to oil-based drilling fluids, known as oil-muds, and especially those oil muds in the form of an invert emulsion.

Invert emulsions are water-in-oil emulsions in which water is dispersed in spherical form by violent agitation of an oil and water mixture in the presence of an emulsifier. In the preparation of oil muds, clay and other minerals are generally present, together with an oil such as a diesel oil or a mineral oil, and water which may range from fresh water to water containing a considerable amount of calcium chloride. Most oil muds use a calcium or magnesium fatty acid soap as the primary emulsifier. Supplemental emulsifiers, generally polyamides, are used for high temperature water and water which contains calcium chloride.

Tall oil compounds are well known as a base for invert emulsifiers. Tall oil is a by-product of the wood pulp industry, containing rosin acids and $C_{18}$ acids such as oleic and linoleic acids. The most popular emulsifiers are the calcium and heavy metal soaps of rosin acids, fatty acids, fatty amines and fatty amides. The amines are quite advantageous at temperatures above 125° F., as they adsorb on the clay surface to prevent breaking of the emulsions and form clay-amine complexes which resist water wetting. These complexes also develop gel strength and reduce the fluid loss of the mud.

Several methods are known for the formation of invert emulsifiers from fatty acid, such as tall oil fatty acids. Thus, according to U.S. Pat. No. 4,508,628, a polyalkylene polyamine is reacted with a mixture of fatty acids containing at least 50% by weight of $C_{18}$ fatty acids, and the reaction product is then reacted with a dicarboxylic acid having from 4 to 8 carbon atoms.

According to U.S. Pat. No. 2,946,746, a polyamide emulsifying agent is prepared by reacting a polyalkylene polyamine which is at least a triethylene tetramine, with a monobasic fatty acid.

U.S. Pat. No. 3,259,572 discloses a drilling fluid containing an emulsifier which is a reaction product of a branched polyamine with an acylating agent such as a higher carboxylic acid.

SUMMARY OF THE INVENTION

It is an object of the present invention to prepare an invert emulsifier for oil-base drilling muds from tall oil fatty acids.

It is a further object of the present invention to prepare an invert emulsifier based on amides which are useful in oil-base drilling muds at high temperatures.

To attain these and other objects, the present invention provides a method for preparing an invert emulsifier for oil-base drilling muds comprising reacting one or more tall oil fatty acids with acrylic acid, fumaric acid, or maleic anhydride, and reacting the product of this reaction with diethylene triamine and one or more tall oil fatty acids to give the invert emulsifier of the present invention. This second reaction may take place in one step or in stages, with the diethylene triamine reaction first, and the tall oil fatty acid reaction subsequently.

DETAILED DESCRIPTION OF THE INVENTION

The present invert emulsifiers are based on the sequence of reactions of diethylene triamine with a particular fatty acid or fatty acid anhydride to give a fatty amide, which is subsequently reacted with a fatty acid. The particular reactive fatty acid or fatty acid anhydride used is prepared by the reaction of one or more tall oil fatty acids with acrylic acid, fumaric acid, or maleic anhydride.

Tall oil includes a mixture of fatty acids, rosin acids and unsaponifiable matter. The fatty acids which generally make up 50 to 60% of the tall oil include conjugated linoleic acid and oleic acid. One or more of these fatty acids will generally take part in the reaction according to the present invention.

When the fatty acid undergoing the reaction with acrylic acid, maleic anhydride, or fumaric acid is conjugated linoleic acid of the following formula:

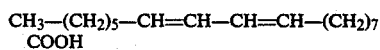

the reaction which takes place is a well-known 1,4-cyclo-addition known as the Diels-Alder reaction. When fumaric acid is the reactant, the reaction product is a triacid of the following formula:

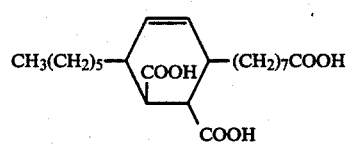

along with oleic and elaidic acids.

When maleic anhydride is the reactant, the reaction product is a triacid anhydride having the following formula:

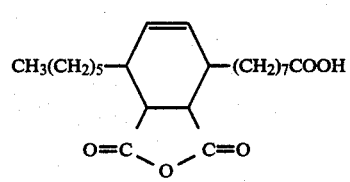

along with oleic and elaidic acids.

When acrylic acid is the reactant, the reaction product is a dicarboxylic acid having the following formula:

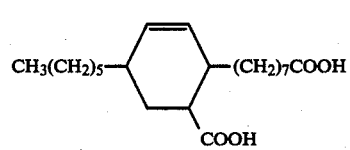

Oleic and elaidic acids are stereoisomeric $C_{18}$ acids having the following general formula:

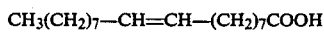

$$CH_3(CH_2)_7-CH=CH-(CH_2)_7COOH$$

As these acids contain only one double bond, they do not undergo the Diels-Alder reaction but instead undergo an addition of the acid or anhydride at the carbon atom next to the one which is double bonded, to give compounds such as:

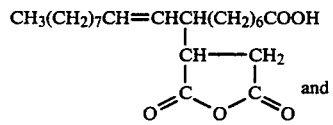

(IVa)

(IVb)

In the subsequent reaction, the fatty acid or fatty acid anhydride may be reacted with diethylene triamine to produce a mixture of fatty amides and imides. When, for example, the anhydride II is reacted, the imide is most probably one of the following general formulas:

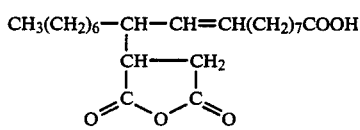

(Va)

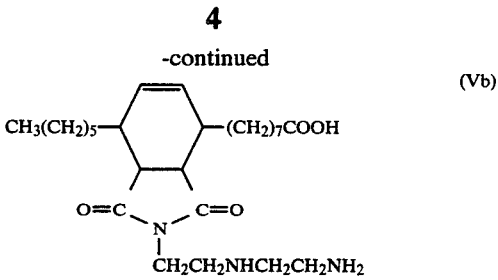

(Vb)

The oleic acid and elaidic acid accompanying the triacid anhydride (II) will form a mixture of amidoamine (Vc) and imidazbline (Vd) of the following formula:

$$CH_3(CH_2)_7CH=CH-(CH_2)_7CONHCH_2CH_2NHCH_2CH_2NH_2$$ (Vc)

and (Vd)

$$CH_3(CH_2)_7CH=CH-(CH_2)_7C\begin{matrix}N-CH_2\\ \\N-CH_2\\ |\\CH_2CH_2NH_2\end{matrix}$$

The amide is then reacted with one or more tall oil fatty acids as discussed above, to produce the invert emulsifier of the present invention. Chemically, the invert emulsifier is mainly a mixture of triacid-fatty acid amidoimidoimines such as (VIa), fatty acid diamides such as (VIb) and some unreacted tall oil fatty acids.

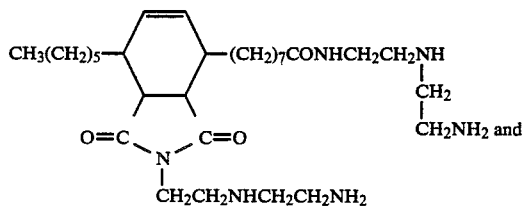

(VIa)

(or linoleic acid)

(or linoleic acid)

$$CH_3(CH_2)_7CH=CH(CH_2)_7CONHCH_2CH_2NHCH_2CH_2NHCO(CH_2)_7CH=CH(CH_2)_7CH_3$$ (VIb)

It is apparent that formula VIa represents the emulsifier components when the initial reaction involves linoleic acid and maleic anhydride (Va) and structure VIb is the result when the amidoamine (Vc) reacts with additional oleic (or elaidic) acid. It naturally follows that where the subsequent reaction with a fatty acid involves Vb, the product is

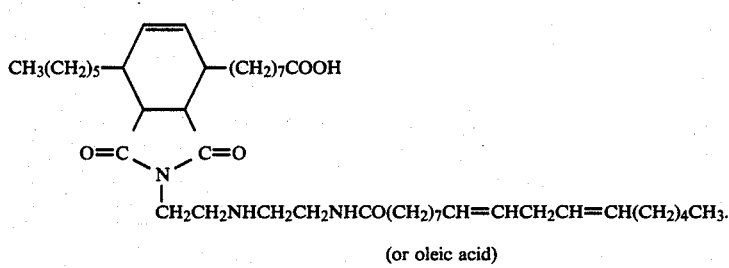

(VII)

(or oleic acid)

Also, where the initial reactants are linoleic acid and either fumaric acid (I) or acrylic acid (III) it follows that the subsequent reactions with diethylene triamine and a fatty acid produce, respectively, Of course, if the initial fatty acid reactant is oleic acid and maleic anhydride producing structure, IVa, the invert emulsifier product will be either

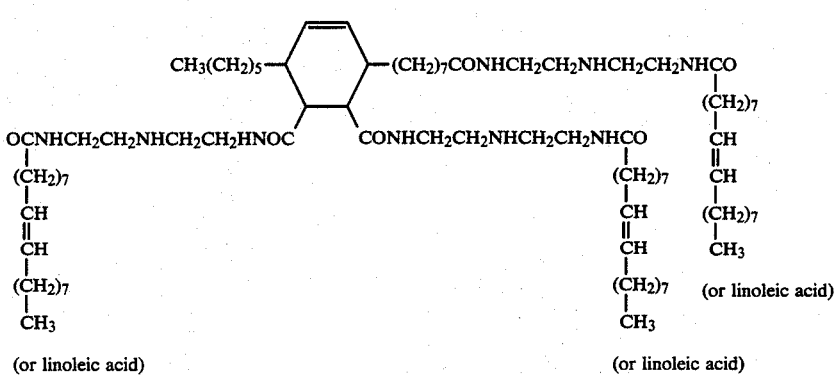

(VIIIa)

and

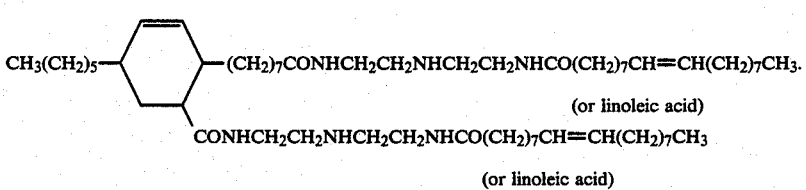

(VIIIb)

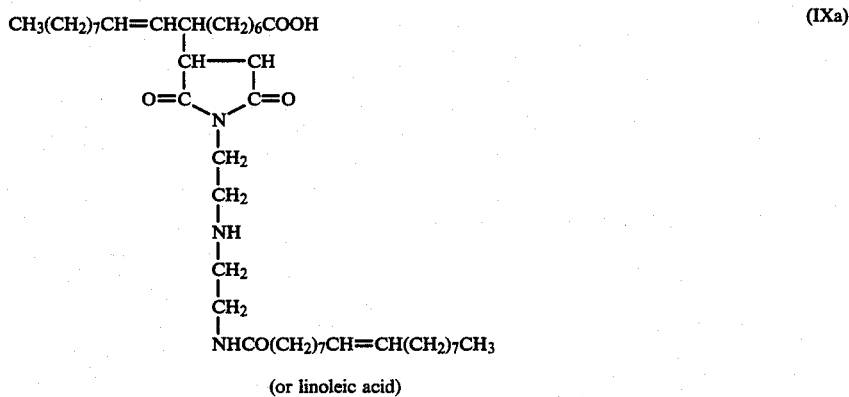

(IXa)

or

-continued

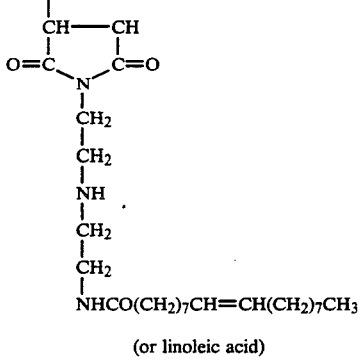

(or linoleic acid)

NHCO(CH₂)₇CH=CH(CH₂)₇CH₃

(or linoleic acid)

All of the reactions described above are moderately high temperature reactions, with the maleic anhydride or fumaric acid reaction generally taking place at 200° to 220° C. for two to four hours and the diethylene triamine reaction generally taking place at about 200°–265° C. The subsequent fatty acid reaction takes place at about 220° C.

In an alternative method for preparation of the invert emulsifier, the reaction product of the tall oil fatty acids with maleic anhydride, fumaric acid or acrylic acid (e.g., I, II or III) is mixed with one or more tall oil fatty acids. This mixture is then reacted with diethylene triamine at about 200°–265° C. to obtain the invert emulsifier.

The present invention is explained further in the following examples.

EXAMPLE 1

In a three-necked flask equipped with thermometer and condensor, 280 g of a tall oil fatty acid consisting essentially of conjugated linoleic acid and oleic acid, and having the designation L-5, was reacted with 50 g maleic anhydride. 0.2% iodine was added as a catalyst, and the mixture was heated to 200° to 220° C. for two hours. The reaction product included a triacid anhydride of formula II, oleic acid and elaidic acid.

EXAMPLE 2

Example 1 was repeated with the exception that the fatty acid was a mixture of oleic and elaidic acids under the designation 1483, and the iodine was omitted. The reaction was run for four hours, and the resultant product was an adduct of formulas (IVa) and (IVb) and unreacted starting fatty acids.

EXAMPLE 3

Example 1 was repeated with the exception that the maleic anhydride was replaced 40 g fumaric acid. The result was a mixture of a triacid according to formula I, oleic acid and elaidic acid.

EXAMPLE 4

150 g of the reaction product of Example 1 was mixed with 50 g diethylene triamine and heated to 260° C. in a three-necked flask until all the condensate was collected. After cooling to 180° C., 160 g of L-5 fatty acid was added to the flask which was reheated to 220° C. After no more condensate was formed, the flask was cooled to 140° C., and xylene was added. The final mixture contained 70% invert emulsifier and 30% aromatic solvent. The invert emulsifier exhibited an amine value of 65.6 and an acid number of 38.9.

EXAMPLE 5

Example 4 procedure was repeated, with the exception that the reaction product of Example 1 was replaced with the reaction product of Example 2. The resultant invert emulsifier had an amine number of 60.1 and an acid number of 39.1.

EXAMPLE 6

The procedure of Example 4 was repeated with the exception that the reaction product of Example 1 was replaced with the reaction product of Example 3. An invert emulsifier was produced with an amine value of 31.5 and an acid number of 70.6.

EXAMPLE 7

150 g of the reaction product of Example 3 was blended with 150 g of the fatty acid L-5 and the mixture reacted with 35 g diethylene triamine at a temperature of 220° C. The reaction mixture was then cooled as described in Example 4. The invert emulsifier product had an amine value of 44 and an acid number of 61.1.

EXAMPLE 8

The procedure of Example 4 was repeated with the exception that the reaction product of Example 1 was replaced by 250 g of the addition product of acrylic acid to L-5, commercially available as Westvaco Diacid®1525, containing about 40% of the dicarboxylic acid (III), and reacted with 30 g diethylene triamine at a temperture of 220° C. The invert emulsifier produced has an amine value of 54 and an acid number of 58.9.

EXAMPLE 9

The procedure of Example 4 was repeated with the exception that the reaction product of Example 1 was replaced by dicarboxylic acid (III), commercially available as Westvaco Diacid®1550, and reacted with diethylene triamine at a temperature of 220°–265° C. and subsequently reacted with tall oil fatty acid. Thus, 125 g Westvaco Diacid®1550 was heated with 35 g diethylene triamine to 265° C. until 12 ml distillate was collected. After cooling to 180° C., 175 g tall oil fatty acid was added and the mixture was heated to 220° C. to obtain an invert emulsifier with the amine value of 33.0 and an acid number of 73.3

EXAMPLE 10

The invert emulsifiers of Examples 4 through 9 were used to prepare 12 pound per gallon drilling muds of the following composition:

| Diesel Oil | 0.73 | bbl |
|---|---|---|
| Water | 0.07 | bbl |
| Calcium chloride | 12 | lb/bbl |
| Geltone II (organophilic clay) | 8 | lb/bbl |
| Barite (Barium sulfate) | 245 | lb/bbl |
| Emulsifier | 11 | lb/bbl |

The rheology, electrical stability and API filter loss were measured initially. After hot rolling for sixteen hours at 350° F., the above tests were repeated and HP, HT filter loss at 300° F. was also measured. The results of the final evaluation are shown in the following table. The six emulsifiers performed quite similarly. The muds had filtrates from the HP,HT filter loss with a small amount of water. Another indication of the good performance was the high value from the electrical stability reading.

TABLE

| Invert Emulsifier Prepared From | Ex. 4 L-5 Maleic Anhydride | Ex. 5 1483 Maleic Anhydride | Ex. 6 L-5 Fumaric Acid | Ex. 7 L-5 Fumaric Acid | Ex. 8 L-5 Acrylic Acid | Ex. 9 L-5 Acrylic Acid |
|---|---|---|---|---|---|---|
| Apparent Viscosity, cp, 90° F. | 42 | 40 | 38.5 | 52 | 72.5 | 40 |
| Plastic Viscosity, cp, 90° F. | 33 | 31 | 30 | 36 | 44 | 30 |
| Yield Point, lb/100 ft² | 18 | 18 | 17 | 32 | 57 | 20 |
| Gel Strength, lb/100 ft², 10 sec/10 min. | 11/16 | 11/15 | 10/18 | 14/17 | 27/39 | 9/15 |
| Electrical Stability, Volts, 90° F. | 2,000+ | 2,000+ | 1,780 | 1,572 | 2,000 | 1,044 |
| API Filter Loss, mL/30 min. | 3.0 | 3.0 | 4.0 | 5.2 | 5.0 | 3.0 |
| HP, HT Filter Loss, mL/30 min. 300° F. | 22.4 oil 2.0 water | 23 + trace water | 36 | 28 | 24 | 17+ (2 emulsions) |

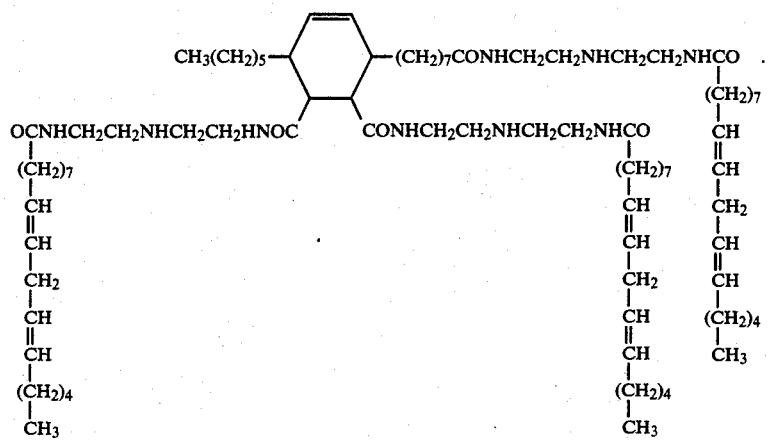
15. The invert emulsifier of claim 9 wherein the triacid-fatty acid amidoimidoamines comprise
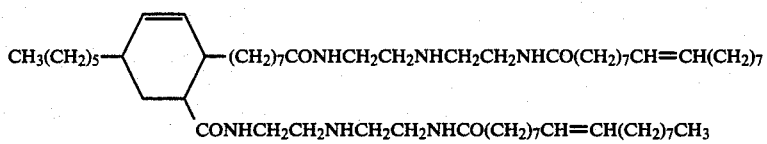
or
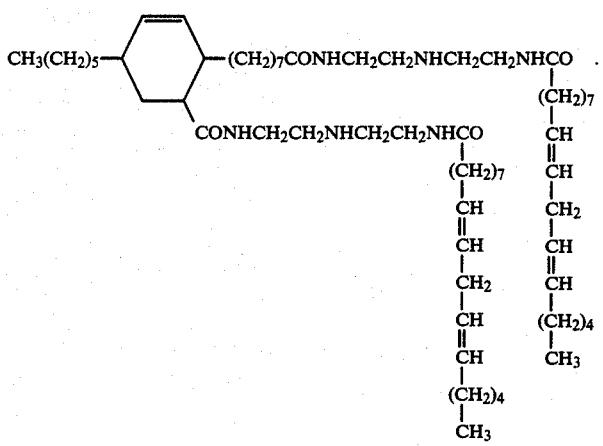
16. The invert emulsifier of claim 9 wherein the triacid-fatty acid amidoimidoamines comprise
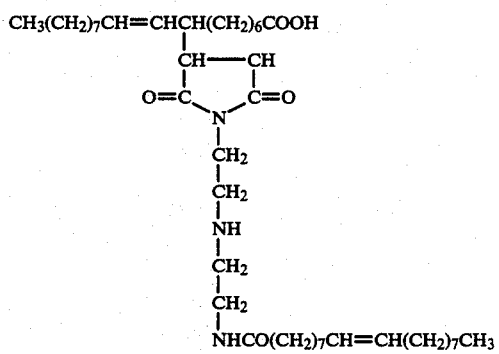
-continued
or
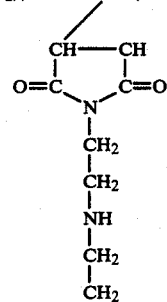
17. The invert emulsifier of claim 9 wherein the triacid-fatty acid amidoimidoamines comprise CH₃(CH₂)CH=CHCH(CH₂)₆CONHCH₂CH₂NHCH₂CH₂NHCO(CH₂)₇CH=CH(CH₂)₇CH₃
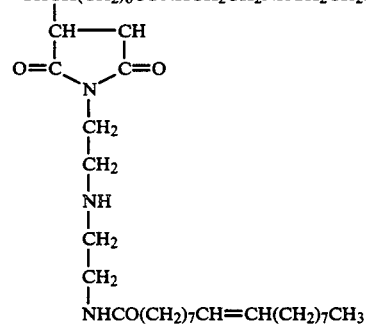
or
CH₃(CH₂)CH=CHCH(CH₂)₆CONHCH₂CH₂NHCH₂CH₂NHCO
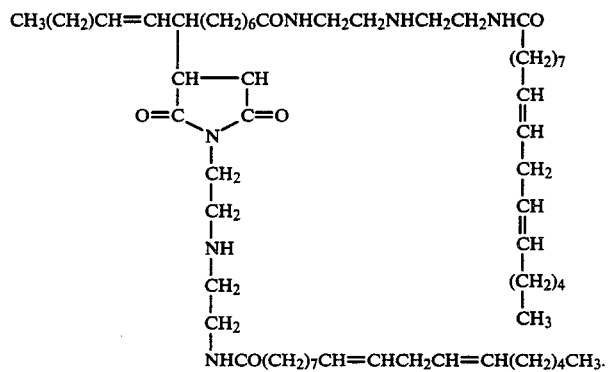

What is claimed is:

1. A process for the preparation of an invert emulsifier for an oil base drilling mud, comprising the steps of:
   (a) reacting a first $C_{18}$ tall oil fatty acid selected from the group consisting of linoleic acid, oleic acid, and a mixture thereof with a member selected from the group consisting of acrylic acid, fumaric acid, and maleic anhydride;
   (b) reacting the product of step (a) with diethylene triamine; and
   (c) reacting the product of step (b) with a second $C_{18}$ tall oil fatty acid selected from the group consisting of linoleic acid, oleic acid, and a mixture thereof to produce the invert emulsifier.

2. The process of claim 1, wherein said tall oil fatty acid includes conjugated linoleic acid and said reaction of step (a) takes place in the presence of iodine as a catalyst.

3. The process of claim 1, wherein the reaction of step (a) takes place at 200° to 220° C. for two to four hours.

4. The process of claim 1, wherein the reaction of step (b) takes place at a temperature of about 220°-265° C.

5. A process for the preparation of an invert emulsifier for an oil base drilling mud, comprising the steps of:
   (a) reacting a first $C_{18}$ tall oil fatty acid selected from the group consisting of linoleic acid, oleic acid, and a mixture thereof with a member of the group consisting of acrylic acid, fumaric acid, and maleic anhydride; and
   (b) reacting a blend of the reaction product of step (a) and a second $C_{18}$ tall oil fatty acid selected from the group consisting of linoliec acid, oleic acid, and a mixture thereof with diethylene triamine to obtain the invert emulsifier.

6. The process of claim 5, wherein said tall oil fatty acid includes conjugated linoleic acid and said reaction of step (a) takes place in the presence of iodine as a catalyst.

7. The process of claim 5, wherein the reaction of step (a) takes place at 200° to 220° C. for two to four hours.

8. The process of claim 5, wherein the reaction of step (b) takes place at a temperature of about 220°-265° C.

9. An invert emulsifier for an oil base drilling mud comprising a mixture of triacid-fatty acid amidoimidoamines, fatty acid diamides, and unreacted tall oil fatty acids.

10. The invert emulsifier of claim 9 wherein the triacid fatty acid amidoimidoamines comprise

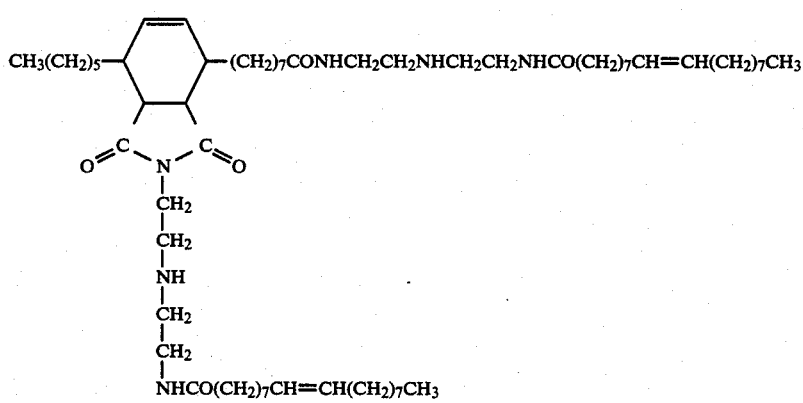

or

-continued

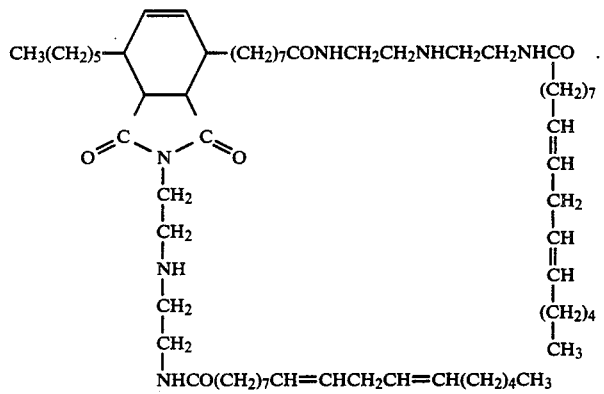

11. The invert emulsifier of claim 9 wherein the fatty acid diamides comprise

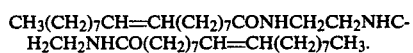

12. The invert emulsifier of claim 10 wherein the fatty acid diamides comprise CH$_3$(CH$_2$)$_7$CH=CH(CH$_2$)$_7$CONHCH$_2$CH$_2$NHCH$_2$CH$_2$NHCO(CH$_2$)$_7$CH=CH(CH$_2$)$_7$CH$_3$.

13. The invert emulsifier of claim 9 wherein the triacid-fatty acid amidoimidoamines comprise

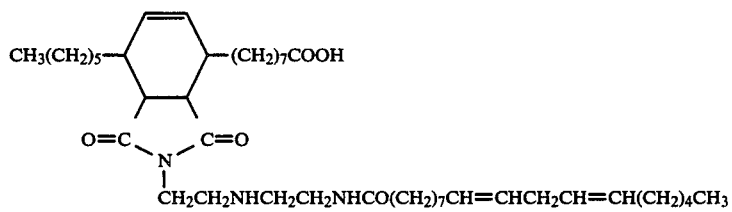

or

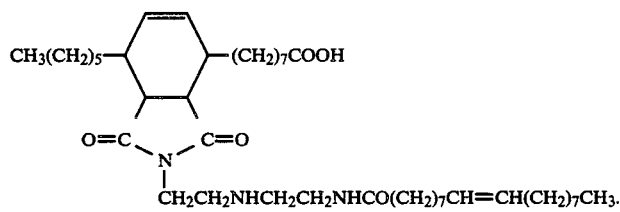

14. The invert emulsifier of claim 9 wherein the triacid-fatty acid amidoimidoamines comprise

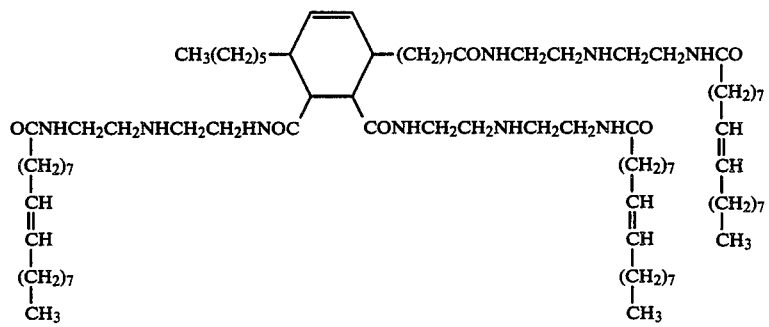

or